(12) United States Patent
Harikrishna et al.

(10) Patent No.: US 9,744,071 B2
(45) Date of Patent: Aug. 29, 2017

(54) METHOD AND DEVICE FOR NON-INVASIVE ANATOMICAL AND SYSTEMIC COOLING AND NEUROPROTECTION

(71) Applicant: The Johns Hopkins University, Baltimore, MD (US)

(72) Inventors: Tandri Harikrishna, Ellicott City, MD (US); Menekhem Muz Zviman, Belcamp, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 958 days.

(21) Appl. No.: 13/751,617

(22) Filed: Jan. 28, 2013

(65) Prior Publication Data

US 2013/0204331 A1  Aug. 8, 2013

Related U.S. Application Data

(63) Continuation-in-part of application No. 13/579,370, filed as application No. PCT/US2011/025121 on Feb. 16, 2011, now Pat. No. 9,629,745.
(Continued)

(51) Int. Cl.
*A61F 7/00* (2006.01)
*A61F 7/12* (2006.01)

(52) U.S. Cl.
CPC .... *A61F 7/0085* (2013.01); *A61F 2007/0065* (2013.01); *A61F 2007/0069* (2013.01); *A61F 2007/126* (2013.01)

(58) Field of Classification Search
CPC ...... A61F 2007/0065; A61F 2007/0067; A61F 2007/0068
See application file for complete search history.

(56) References Cited

U.S. PATENT DOCUMENTS 4,718,429 A * 1/1988 Smidt .................. A61F 7/10
607/104
6,354,099 B1 * 3/2002 Bieberich ............ A61F 7/0097
607/104
(Continued)

FOREIGN PATENT DOCUMENTS

CN  1946359 A  4/2007
WO  01/76655 A2  10/2001
(Continued)

OTHER PUBLICATIONS

Search Report dated Oct. 24, 2014 for EP Application 11745187.2.
Examination Report dated Aug. 21, 2014 for Chinese Patent Application No. 201180000972 4.7.

*Primary Examiner* — Kaitlyn Smith
(74) *Attorney, Agent, or Firm* — Johns Hopkins Technology Ventures

(57) ABSTRACT

The present invention provides a method and device for non-invasive anatomical and systemic cooling, fluid removal and/or energy removal. The present invention provides for removal of fluid and cooling of various bodily fluid-containing spaces or surfaces, such as mucus-containing spaces or surfaces via delivery of a dry fluid not including a coolant into or upon the mucus-containing space or surface. Exposure of mucus to the dry fluid yields evaporation of body fluid, removal of energy, cooling of the anatomical feature, and systemic cooling. Therefore, therapeutic hypothermia may be achieved for neuroprotection of various organs after ischemic insult, like the brain after cardiac arrest. Similarly, excess fluid removal is achievable for treatment of cardiogenic shock or other conditions that cause significant fluid build-up, especially in cases of compromised renal function. Additionally, the invention may be used to reduce fever, and other conditions where removal of heat, energy and/or water are beneficial.

3 Claims, 9 Drawing Sheets

Related U.S. Application Data

(60) Provisional application No. 61/305,038, filed on Feb. 16, 2010, provisional application No. 61/315,218, filed on Mar. 18, 2010, provisional application No. 61/590,844, filed on Jan. 26, 2012.

(56) References Cited

U.S. PATENT DOCUMENTS

| | | | | |
|---|---|---|---|---|
| 6,519,964 B2* | 2/2003 | Bieberich | | A61F 7/0097 607/104 |
| 7,527,612 B1* | 5/2009 | Carpenter | | A61F 7/02 604/291 |
| 7,824,436 B2* | 11/2010 | Barbut | | A61F 7/12 607/1 |
| 7,837,722 B2* | 11/2010 | Barbut | | A61F 7/12 607/104 |
| 8,075,605 B2* | 12/2011 | Barbut | | A61F 7/12 607/1 |
| 8,100,123 B2* | 1/2012 | Belson | | A61F 7/0085 128/200.14 |
| 8,313,520 B2* | 11/2012 | Barbut | | A61F 7/12 607/1 |
| 8,480,723 B2* | 7/2013 | Barbut | | A61F 7/12 607/105 |
| 8,721,699 B2* | 5/2014 | Barbut | | A61F 7/12 607/105 |
| 8,932,339 B2* | 1/2015 | Harikrishna | | A61F 7/12 607/104 |
| 2002/0056281 A1* | 5/2002 | Bieberich | | A61F 7/0097 62/259.3 |
| 2003/0079488 A1* | 5/2003 | Bieberich | | A61F 7/0097 62/259.3 |
| 2004/0064171 A1* | 4/2004 | Briscoe | | A61F 7/02 607/104 |
| 2006/0003688 A1 | 1/2006 | Turner | | |
| 2006/0058859 A1* | 3/2006 | Merrill | | A61F 7/12 607/105 |
| 2006/0276552 A1* | 12/2006 | Barbut | | A61F 7/12 514/743 |
| 2007/0021808 A1 | 1/2007 | Rojas | | |
| 2007/0123813 A1* | 5/2007 | Barbut | | A61F 7/12 604/19 |
| 2008/0004613 A1* | 1/2008 | Barbut | | A61F 7/12 606/21 |
| 2008/0249188 A1* | 10/2008 | Barbut | | A61F 7/12 514/759 |
| 2010/0211140 A1* | 8/2010 | Barbut | | A61F 7/12 607/105 |
| 2011/0028938 A1* | 2/2011 | Barbut | | A61F 7/12 604/514 |
| 2012/0083764 A1* | 4/2012 | Barbut | | A61F 7/12 604/514 |
| 2013/0073015 A1* | 3/2013 | Rozenberg | | A61F 7/0085 607/106 |
| 2013/0103126 A1* | 4/2013 | Harikrishna | | A61F 7/12 607/105 |
| 2013/0204331 A1* | 8/2013 | Harikrishna | | A61F 7/0085 607/107 |
| 2014/0053834 A1* | 2/2014 | Harikrishna | | A61F 7/12 128/203.12 |
| 2014/0205554 A1* | 7/2014 | Beckman | | A61F 7/00 424/65 |
| 2014/0343641 A1* | 11/2014 | Barbut | | A61F 7/12 607/105 |

FOREIGN PATENT DOCUMENTS

| | | |
|---|---|---|
| WO | 2006/124702 A2 | 11/2006 |
| WO | 2011/115964 A1 | 9/2011 |

* cited by examiner

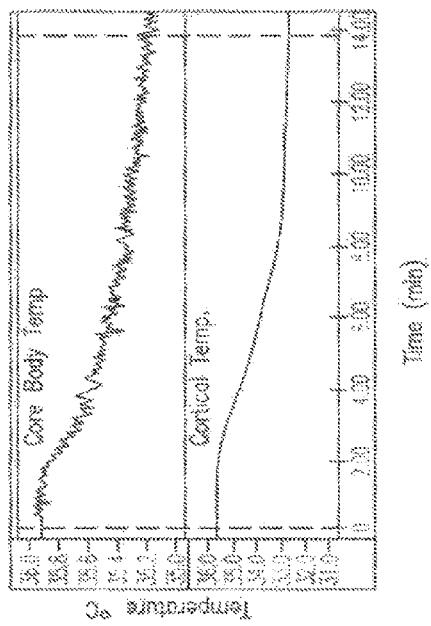
FIG. 11
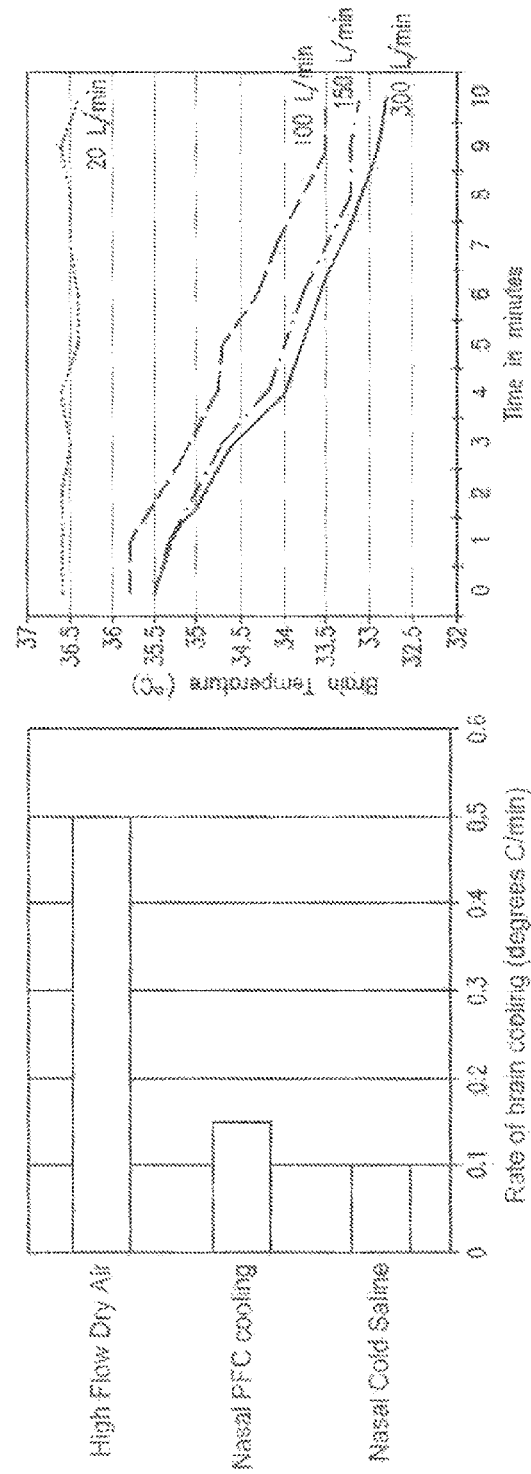
FIG. 13
FIG. 12

METHOD AND DEVICE FOR NON-INVASIVE ANATOMICAL AND SYSTEMIC COOLING AND NEUROPROTECTION

CROSS REFERENCE TO RELATED APPLICATIONS

This application is a continuation-in-part of U.S. patent application Ser. No. 13/579,370 filed on Jan. 9, 2013, which is a 35 U.S.C. §371 U.S. national entry of International Application PCT/US2011/025121 having an international filing date of Feb. 16, 2011, which claims the benefit of U.S. Provisional Application No. 61/305,038 filed Feb. 16, 2010 and 61/315,218 filed Mar. 18, 2010. This application also claims the benefit of U.S. Provisional Patent Application No. 61/590,844, filed on Jan. 26, 2012. The content of each of the aforementioned applications is herein incorporated by reference in their entirety.

BACKGROUND OF THE INVENTION

Field of the Invention

The invention relates generally to methods and devices for removing heat, energy, and/or fluid from a living mammal. In particular, this invention relates to a method and device for controlled delivery of gas to the nasopharyngeal cavity, lungs or other anatomical feature of a mammal. The invention also relates to therapeutic methods for using the method and device to provide cerebral cooling, systemic cooling, and neuroprotection via such cooling. The invention further relates to methods for using the methods and device to remove excess fluid from the body in cases of cardiogenic shock and other conditions which result in the accumulation of excess fluid. The invention additionally relates to methods for removing energy from the body, for increasing metabolic rate, and for promoting weight loss.

Background Information

Removal of heat, energy, and/or fluid from a body is a proven therapeutic requirement for many critical and non-critical health conditions. Such conditions include cardiac arrest, refractory heart failure, stroke, sport or combat related overheating, heat cramps, heat exhaustion, heat stroke, compromised renal function, obesity, and many others. For each of these conditions, there is a continuing need for non-invasive therapies to remove heat, fluid and/or energy from the body.

Cardiac arrest (CA) is a leading cause of morbidity and mortality in the developed world. Resuscitation is attempted in an estimated 400,000 patients annually in the United States and 66 per 100,000 population every year in Europe. Recovery without residual neurologic damage after cardiac arrest with global cerebral ischemia is rare. Of the few that survive to hospital discharge, >50% are left with permanent neurological sequelae. After cardiac arrest with no blood flow for more than five minutes, the generation of free radicals, during reperfusion, together with other mediators, creates chemical cascades that result in cerebral injury. Several studies have shown that moderate systemic hypothermia (30° C.) or mild hypothermia (34° C.) markedly mitigates brain damage after cardiac arrest in dogs. Two well-conducted rand3mized clinical trials demonstrated the benefit of cooling survivors of witnessed CA who had ventricular fibrillation (VF) as the presenting rhythm. Based on these data, the American Heart Association and the European Resuscitation Council recommend therapeutic hypothermia (TH) in the management of unconscious patients following CA.

Despite the strong experimental and clinical evidence, the use of TH is at best sporadic, with less than 10% of the eligible CA patients receiving hypothermia. Animal studies suggest that cooling early after ROSC is associated with improved neurological outcome and a delay in initiation of hypothermia is associated with decreased benefit. One of the important factors in rapid induction of TH is the unavailability of a reliable, easy to implement method in the field that does not interfere with resuscitation attempts. Current out-of-hospital methods to induce TH include ice-cold saline IV, ice packs, cooling blankets, and cooling helmets, which are ineffective to induce hypothermia. As such, there is an enormous need for a method to induce TH in the out-of-hospital setting that is non-invasive, rapid, effective, and without major harmful side effects.

The ability to induce hypothermia non-invasively and in a timely fashion is of enormous clinical value not only in cardiac arrest, but also in all threatened ischemic insults including cerebrovascular ischemia, traumatic brain injury, spinal cord injury, neonatal encephalopathy and coronary artery disease. In cardiac arrest alone, TH will save an additional 7,500 lives per year with 50 patients treated per life saved. Post-CA patients receiving TH gain an average of 0.66 quality-adjusted life years at an incremental cost of $31,254 due to the extended hospital stay, which has comparable cost-effectiveness per quality-adjusted life year to many economically acceptable health care interventions.

Investigators have tried cooling the body through the nasal passages using non-compressed, low-flow air/oxygen and observed the hypothermic effect, although the mechanism behind the effect was not well understood. For example, the RhinoChill™ device achieves cooling by evaporating a coolant perfluorocarbon (PFC) in the airway or by using a volatile gas to evaporate water vapor introduced into the air to decrease the air temperature in the nasal cavity. Evaporation of the coolant PFC in the nose reportedly results in convective cooling of the brain and core body temperature.

However, ambulatory hypothermia methods relying on direct heat exchange using either cold perfusates (coolants) or surface cooling by evaporation of a volatile substance can produce excessively extreme local cooling of the exposed surfaces, at some risk to the patient. As such, such active cooling therapies are to be administered by specially trained medical technicians.

In conditions of cardiac stress, a patient will build up excess water in the extremities. Presently, the primary way to remove water from the body is via urination by the use of diuretic drugs. This method can take a significant period of time, and may not be useful especially in patients with compromised renal conditions.

Additionally, there is a need for augmented body cooling in cases of combat and sports related overheating due to exertion and adverse ambient conditions.

Furthermore, there is a need to remove energy (calories) from a body as a means to augment weight loss.

Thus, a need exists for a minimally or non-invasive method to remove heat, fluid and/or energy without use of coolants or volatile substances for instance, which preferably can be used in non-medical settings, without supervision by specially trained personnel.

SUMMARY OF THE INVENTION

The present invention provides a minimally or non-invasive method and device to provide passive anatomical, systemic cooling, fluid extraction, energy extraction, metabolic rate increase and/or weight loss, by utilizing the nasal heat loss mechanism wherein heat and fluid is lost intentionally by the body due to its natural response to humidify and condition the inspired air.

As such, in one aspect, the invention provides a method of passively cooling an anatomical feature in a mammal by controlled, induced evaporation of a bodily fluid from a bodily fluid-containing space or surface, such as a mucus containing-space or surface in the mammal. The method includes delivering a dry fluid (compressed or not) which does not include a coolant (i.e., a refrigerant or chilled fluid) into or upon the bodily fluid-containing space or surface to provide controlled evaporation and transport (removal) of the bodily fluid upon contact with the dry fluid. Such evaporation and transport of the bodily fluid produces cooling of the anatomical feature and systemic cooling, as well as body fluid elimination. In one embodiment, the fluid is a gas.

According to the cooling aspect of the invention, the invention provides methods for reducing overheating and providing comforting and/or therapeutic cooling in cases of heat related stress, including overheating resulting from sport and/or combat activities, fever, heat exhaustion and heat stroke.

The invention also provides a method for removing excess body fluids in cases where removal of fluids is useful in the treatment of certain conditions including refractory heart failure, in which the body retains fluid in extremities.

In cases where there is not a need to cool the body or remove excess heat or fluid, the invention provides a method for the extraction of fluid and energy, promoting weight loss.

In various embodiments, the gas is dehumidified prior to delivery to the bodily fluid-containing space or surface for cooling of the targeted anatomical feature. In various embodiments, the fluid has a relative humidity before delivery to the mammal of less than or equal to about 90, 80, 70, 60, 50, 40, 30, 20, or 10%. In various embodiments, the gas is delivered at a flow rate of greater than about 10 L/min, such as a flow rate of between about 20 and 200 L/min, 40 and 130 L/min, 20 and 80 L/min, or 40 and 500 L/min.

According to metabolic rate increase and weight loss embodiments, system of the invention may be used overnight over extended periods of time, and the flow rate is preferably set at a lower range, for example between about 10 and 40 L/Min, to improve long term tolerability.

Where cooling is not required or desired and in cases of fluid extraction applications, the gas may be warmed to increase fluid extraction. According to this embodiment, the gas may be warmed to body temperature, or >30° C., >40° C. or greater than >50° C.

In various embodiments, the fluid is delivered to a bodily fluid-containing surface or cavity, such as the nasal cavities (nasopharynx and nostrils), oral cavity, lungs, trachea, gastro-intestinal system, stomach, and urogenital cavity and mucus surfaces. According to one cooling embodiment, the anatomical feature is the brain or brain stem, and delivery of the fluid is made to the nasal cavities. In one embodiment, the gas is delivered for a duration to lower core body temperature of the mammal between about 2 to 4° C. In an especially preferred embodiment, the mammal is a human.

Conveniently, the susceptibility of the invention to practice with uncompressed fluid (such as ambient air) lends it to use with relatively simple air delivery devices, such as respiratory masks or nebulizers. The device may be portable and may also be configured to optionally work via battery power. The invention is therefore particularly well-suited to use in ambulatory therapies, including emergency settings, combat settings, sport settings, and even clinic and home-use settings. In a particularly preferred embodiment, the gas is delivered via a device of the present invention.

Accordingly, the present invention further provides a device for cooling an anatomical feature in a mammal, providing systemic cooling in a mammal, removing excess fluid from a mammal, raising the metabolic rate of a mammal, and/or promoting weight loss in a mammal, by evaporation of a fluid from a bodily fluid-containing space or surface in the mammal. The device includes: a) a conduit which includes a proximal end, a distal end, a first lumen extending between the proximal and distal ends, and one or more fluid delivery ports at the distal end in fluid communication with the first lumen; and b) a fluid source in fluid communication with the proximal end of the first lumen for supplying a dry fluid not containing a coolant to the first lumen; wherein the device is configured such that fluid flows distally along the first lumen through the fluid delivery ports to contact the bodily fluid-containing space or surface upon expansion of the fluid through the fluid delivery ports. If the dry fluid is compressed, a compressor may be provided to the fluid source; or the fluid may be provided in pre-compressed condition; e.g., in a valved tank or other canister.

In various embodiments, the device further includes: c) a second lumen extending toward the distal end of the conduit; d) one or more return ports at the distal end in fluid communication with the second lumen; and e) an exhaust port in fluid communication with the proximal end of the second lumen; wherein the device is configured such that fluid flows distally along the first lumen through the fluid delivery ports and reenters the second lumen through the return ports.

In some embodiments, the device also further includes one or more temperature sensors (for the fluid and/or the treated mammal), pressure sensor and/or fluid flow regulator. In some embodiments the device includes a third lumen extending toward the distal end of the conduit, and one or more additional fluid delivery ports at the distal end in fluid communication with the third lumen and/or the exhaust ports. The device may be configured to be lightweight and portable, and may be configured to operate via connection to standard wall socket and/or optionally by onboard rechargeable battery. The device may optionally include a disposable desiccant cartridge and may be provided with optional inputs for receiving air and/or other gases via an external tank.

BRIEF DESCRIPTION OF THE DRAWINGS

Various features and advantages of the disclosure will become more apparent by the following detailed description of several embodiments thereof with reference to the attached drawings, of which:

FIG. 11 is a graphical representation showing the core body temperature (measured in the right atrium) (top) and brain temperature (measured in lateral ventricles) (bottom) during 100 L/min flow of nasal dry air in an intubated adult pig;

FIG. 12 is a graphical plot showing the effects of airflow rate on the change in brain temperature, shown from 20 L/min to 300 L/min; and FIG. 13 is a histogram comparing the rate of brain cooling using various TH techniques.

DETAILED DESCRIPTION OF THE INVENTION

Figure 1:
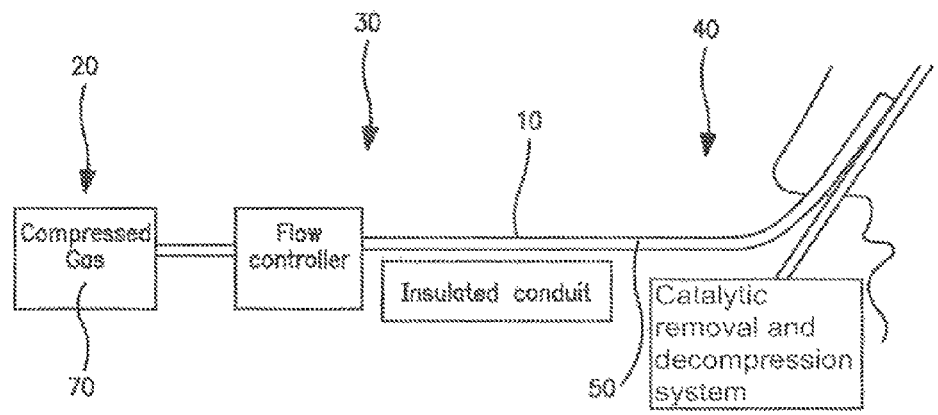
FIG. 1 illustrates a diagram of a cooling device and methodology of the present invention, according to an embodiment.

The contents of all references cited herein are to be considered to be incorporated within this disclosure by this reference.

The nose in mammals has highly convoluted turbinates with extensive vascularization with a subepithelial capillary system, and a distensible, cavernous, vascular network. The turbinates enormously increase the surface area and are richly vascular and capable of engorgement in response to environmental stimuli, especially cold and dry air stimulation. Unidirectional flow of ambient air through the nose results in a 65% increase in nasal mucosal blood flow, an effect that is promptly mitigated by humidification and warming of the inspired air. Moreover, warm dry air results in significant increase in upper airway blood flow as compared to cold dry air hyperventilation, which is subsequently mitigated by humidifying the air. Respiratory water loss also follows a similar paradigm with a water loss of 0.66±0.17 g $H_2O$/min for cold dry air ventilation and 0.90±0.16 g $H_2O$/min for warm dry air hyperventilation for airflow rates of up to 20 L/min. This water loss by the body is in fact heat loss due to the high latent heat of evaporation of water (2.27 kJ/g), which is provided by the nasal blood flow. Unidirectional flow in the nostrils is associated with significant dehydration with water lost during humidification of the inspired air. Experimental testing shows that the rate of water loss by this process is directly associated with heat loss by the body, making humidification an excellent way to extract heat.

In contrast, evaporation of a coolant or volatile gas introduced into the nose reduces evaporation of bodily fluids present (and reduces related water loss). While cooling may result from both evaporative processes, the former path to cooling is less controllable than is cooling resulting from the body's intrinsic response to induced water loss.

The present inventions are based in part on the observation that anatomic and systemic cooling, including therapeutic hypothermia, as well as fluid removal, metabolic rate increase, and weight loss, may be achieved by evaporation of a fluid from a bodily fluid-containing space or surface using high flow dry air applied to the space. The invention is based on the physiological evaporative response to dry fluid, such as gas flow. Introduction of dry air into a bodily fluid-containing space or surface, such as the nasal or nasopharynx cavity causes release of the bodily fluid from membranes, whose subsequent evaporation produces vasodilation, evaporative heat loss and cooling of blood. With regard to the nasal cavity, during normal breathing, energy (via the humidification process) is transferred into the inspired air before entering the lungs. After the inhaled air cycles through the lungs, some of the energy in the air is transferred back into the nasal turbinates during exhalation. However, without being bound to a particular theory, the present method and device bypasses the transfer of energy back in to the nasal turbinates during exhalation. As opposed to other techniques, the present inventions do not utilize coolants, such as refrigerants or chilled fluids, to achieve cooling, heat removal, fluid removal and/or metabolic rate increase.

In contrast to other techniques where exposed surfaces are actively cooled by applying a refrigerant or chilled material to the surface, the present method relies on heat loss directly from the vasculature providing circulation to the tissue of a bodily fluid-containing space or surface with no significant change in surface temperature. For example, the inventors have confirmed that the temperature within the space defined by nostrils exposed to high flow dry gas to nostrils is similar to the inspired air temperature suggesting that the gas does not directly cool the surface of the nasopharynx. This is advantageous over other techniques since generation of extreme cold surface temperatures can be associated with vasoconstriction and shunting of blood flow away from the tissue undermining the effect of surface cooling method. Additionally, without being bound by any particular theory, warm high flow of warm dry air is associated with a greater degree of cooling, an approach which is counterintuitive, but physiologically plausible as warm dry air has been shown to increase respiratory water loss, which then translates to heat loss.

Before the present device and method are described, it is to be understood that this invention is not limited to the particular configuration and method described. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

In one aspect, the present invention provides a non-invasive method to induce TH to provide anatomical and/or systemic cooling. As such, in one aspect, the invention provides a method of cooling an anatomical feature in a mammal by evaporation of a dry fluid from a bodily fluid-containing space or surface in the mammal.

As used herein, "absolute humidity" is used to refer to the amount of water vapor in a gaseous mixture of gas and water vapor as expressed by mass. "Relative humidity" is used to refer to the amount of water vapor that exists in a gaseous mixture of gas and water vapor as a function of its current state, for example temperature. Essentially, relative humidity is a measure of the amount of moisture in the air compared to what the air is capable of holding at a given temperature. In various embodiments, the relative humidity of the gas before being contacted with a bodily fluid is less than or equal to about 90, 80, 70, 60, 50, 40, 30, 20, 10, 5 or 0%. In various embodiments, the relative humidity of the gas after being contacted with a bodily fluid is greater than or equal to about 0, 10, 20, 30, 40, 50, 60, 70, 80 or 90%.

As used herein, a "dry" fluid or gas is used to refer to a fluid or gas that is unsaturated with water vapor or other liquid vapor. In various embodiments, the dry gas has a relative humidity of less than or equal to about 90, 80, 70, 60, 50, 40, 30, 20, 10, 5 or 0%.

As used herein, the term "fluid" refers to dry (dehumidified) fluid which effectuates evaporation. As is recognized by one in the art, all gases are fluids. Accordingly, the term fluid is used interchangeably with the term gas.

In various embodiments, dry gas is used in the method and device of the invention to achieve anatomical cooling, systemic cooling, TH, excess fluid extraction, metabolic rate increase and/or weight loss. Several types of gases are suitable for use with the present invention. Such gases include, but are not limited to air, $NO_2$, $CO_2$, $O_2$, and inert gases, such as He, Ar, and Xe, as well as combinations thereof. In related embodiments, the gas may be an anesthetic, such as $N_2O$ or Xe, or a gas which additionally may have neuroprotective properties and systemic effects to promote systemic cooling, such as vasodilation.

Dry fluids delivered according to the invention do not include a coolant (and may be, but need not be, warmed). As used herein, the term "coolant" includes volatile gases and may include dry ice, liquid nitrogen chilled saline, water, anti-freeze solution, refrigerants, such as fluorocarbons, chlorofluorocarbons (CFCs), hydrochlorofluorocarbons (HCFCs), perfluorocarbons (PFCs), R-134a (1,1,1,2 tetrafluoro ethane), Freon™, and other cooling fluids or refrigerants, or a combination thereof. A coolant may also be considered any fluid chilled to a temperature 10° C. or more below normal body temperature. For humans, a coolant would thus be a fluid chilled to about 27, 26, 25, 24, 23, 22, 21, 20, 19, 18, 17, 16, 15, 14, 13, 12, 11, 10, 9, 8, 7, 6, 5, 4, 3, 2, 1, 0° C. or less.

The dry fluid is provided to the bodily fluid-containing space or surface according to the invention. Contact of the flowing dry fluid with such bodily fluid, for example mucus, results in evaporation and cooling of a targeted anatomical feature (i.e., one to which the dry fluid is directly delivered, or which is in circulatory communication with the delivery site for the dry fluid into a bodily fluid-containing space or surface of the body) and/or systemic cooling (more generalized hypothermia). The evaporation results in fluid loss/elimination and the cooling is a result of the heat transfer. Extended periods of such heat transfer, which can also be characterized as heat loss, will eventually result in an increased rate of metabolism in the same way that the body reacts to cold.

Figure 14:
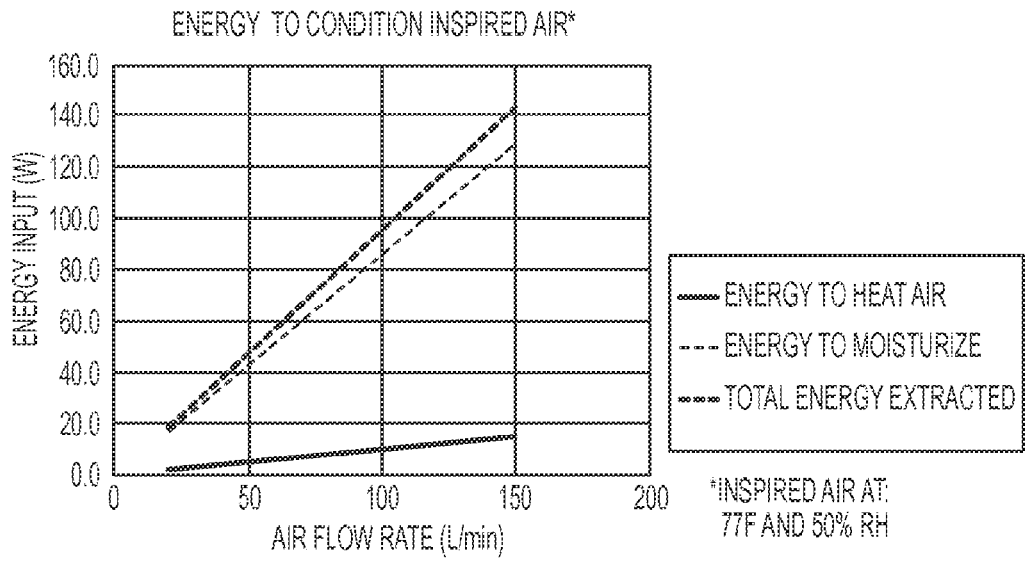
FIG. 14 is a graph showing the energy required by a mammal to condition (heat and moisturize) inspired air to the temperature and humidity appropriate for inhalation to the lungs.

In the normal respiratory process, inspired air is conditioned prior to entering lungs. Air is heated to near body temperature, and is fully humidified. During normal expiration (normal respiration air volumes), moisture used to humidify inspired air is recaptured by the nasal turbinates as a means to conserve energy. FIG. 14 shows the energy required by a mammal to condition inspired air to the temperature and humidity appropriate for normal lung function at varying air flow rates. The lower, black, line shows the energy required to heat air inspired at 77° F. to 86° F.; the middle, blue, line shows the energy required to moisturize air inspired at 50% relative humidity to 100% relative humidity.

Figure 15:
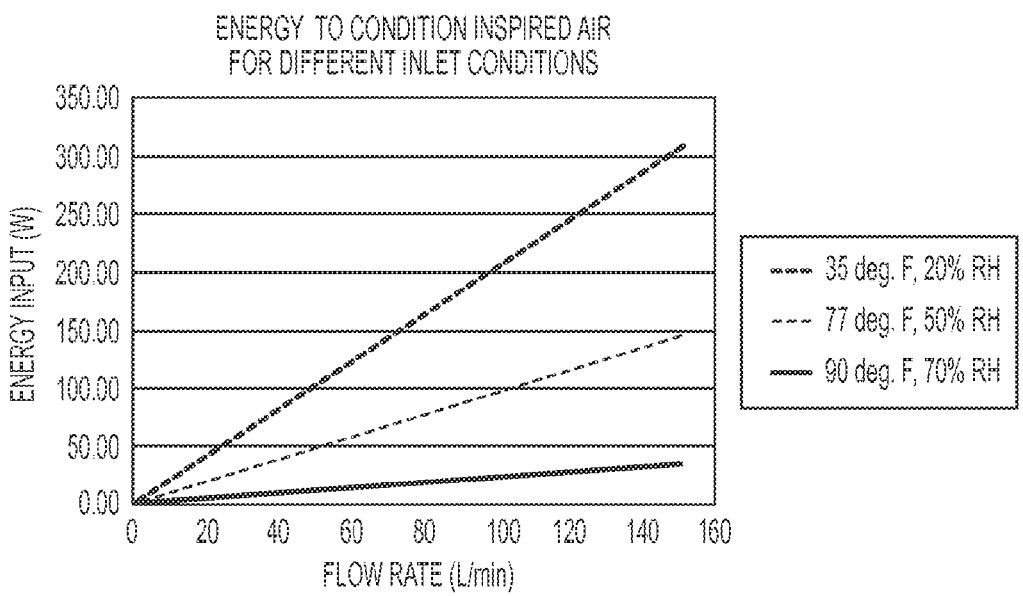
FIG. 15 is a graph showing the energy required by a mammal to condition inspired air at different inlet conditions.

FIG. 15 shows the energy required by a mammal to condition three different inspired air conditions to temperature and humidity appropriate for normal lung function at varying flow rates. The bottom, black, line shows the energy necessary to condition air inspired at 90° F. and 70% relative humidity. The middle, blue, line shows the energy necessary to condition air inspired at 77° F. and 50% relative humidity, and the red line shows the energy necessary to condition air inspired at 35° F. and 20% relative humidity.

Figure 16:
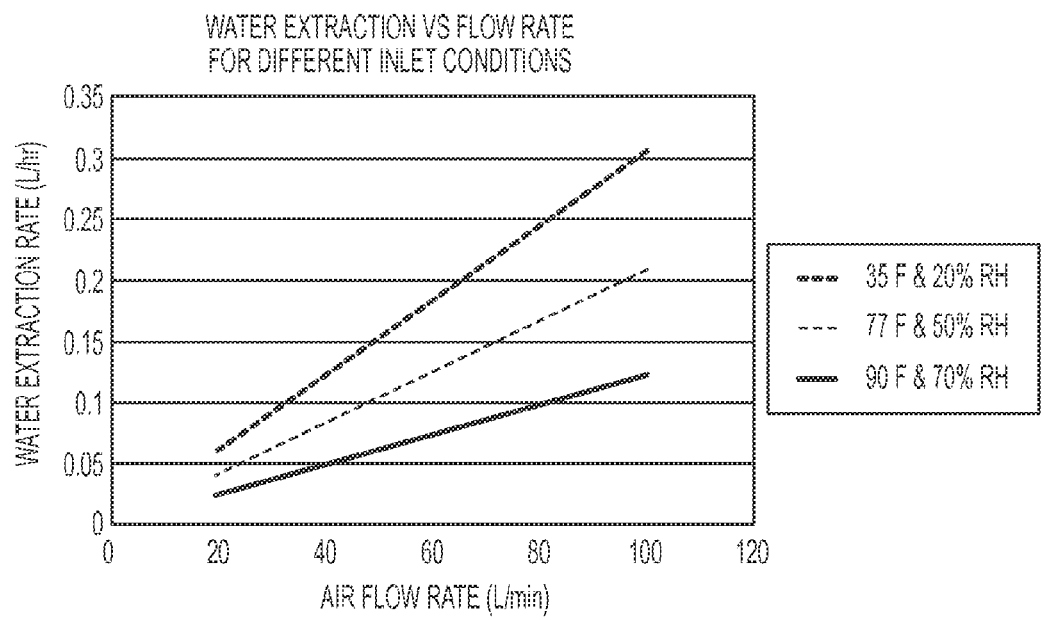
FIG. 16 is a graph showing the water extraction rate according to an embodiment of the present invention versus air flow rate at different inlet conditions.
Figure 17:
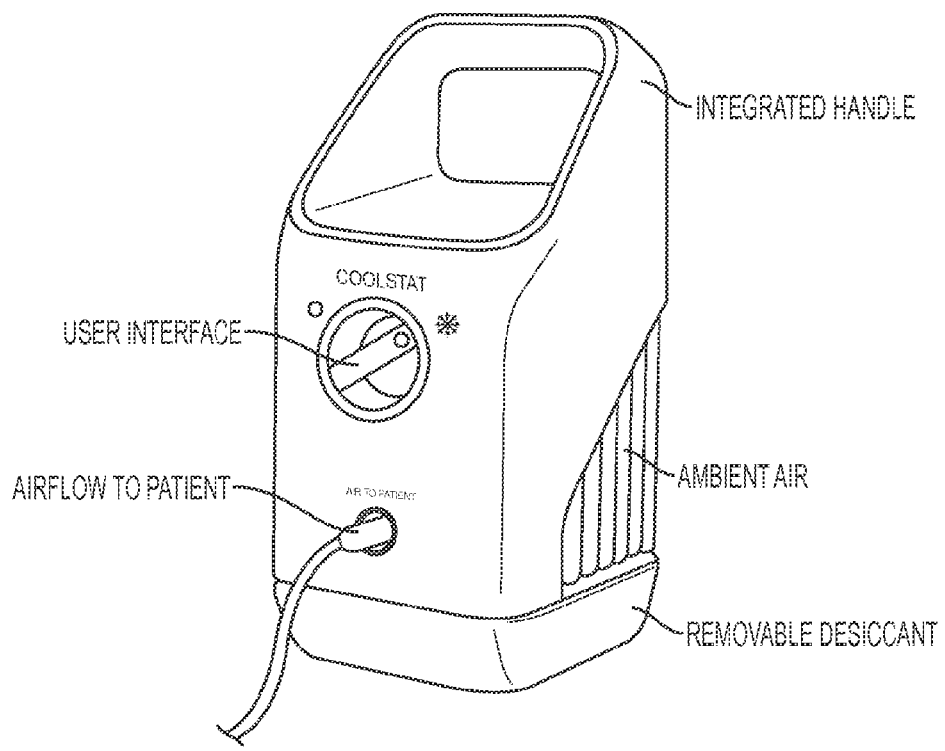
FIG. 17 is a representation of a device according to one embodiment of the invention.

FIG. 16 shows the water extraction versus flow rate for different inspired air conditions. The bottom, black, line shows the water extraction rate versus air flow rate for air inspired at 90° F. and 70% relative humidity. The middle, blue, line shows the water extraction rate versus air flow rate for air inspired at 77° F. and 50% relative humidity, and the red line shows the water extraction rate versus air flow rate for air inspired at 35° F. and 20% relative humidity.

Figure 2:
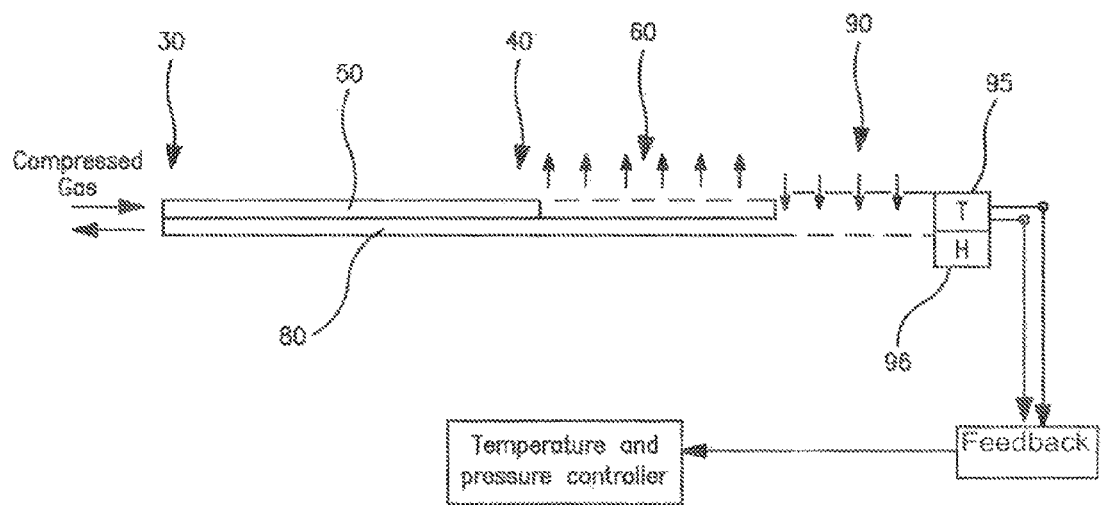
FIG. 2 illustrates a diagram of a portion of a cooling device of the present invention, according to an embodiment.

The method may be performed utilizing a device of the present invention. Accordingly, the present invention further provides a device for 1) cooling an anatomical feature in a mammal, and/or 2) systemic cooling of a mammal, and/or 3) fluid extraction from a mammal, and/or 4) metabolic rate increase, and/or weight loss, by evaporation of a fluid from a bodily fluid-containing space or surface of the mammal. As depicted in FIGS. 1 and 2, the device includes a conduit 10 and a fluid source 20. The conduit 10 has both proximal 30 and distal 40 ends along with a first lumen 50 extending between the proximal 30 and distal 40 ends, and one or more fluid delivery ports 60 at the distal end in fluid communication with the first lumen 50. The fluid source 20 is in fluid communication with the proximal end 40 of the first lumen 30 for supplying a dry fluid 70 not containing a coolant to the first lumen 30. As such, the device is configured such that fluid flows distally along the first lumen 30 through the fluid delivery ports 60 to contact the bodily fluid-containing space or surface. If the dry fluid is a compressed gas, delivery occurs upon expansion of the fluid through the fluid delivery ports, e.g. the nasal cavity.

In various embodiments, the device may further include additional features that allow for the introduced fluid to be exhausted from the bodily fluid-containing cavity. To facilitate removal of the fluid, device further includes a second lumen 80 extending toward the distal end of the conduit 40. The second lumen 80 includes one or more return ports 90 at the distal end in fluid communication with the second lumen 80. As such, fluid that is introduced and expanded through the fluid delivery ports 60 may be allowed to flow out of the bodily fluid-containing space into the second lumen through the return ports via natural flow of the fluid or by applying a suction or negative pressure to the proximal end of the second lumen. The device further includes an exhaust port (e.g. an exhaust manifold) in fluid communication with the proximal end of the second lumen to expel or dissipate the fluid to which suction or a vacuum may be applied. As such, the device is configured such that fluid flows distally along the first lumen through the fluid delivery ports and reenters the second lumen through the return ports after contacting and evaporating fluid, such as mucus within or on the space or surface.

As used herein in reference to optional embodiments, the term "compressed" fluid or gas is used to refer to a fluid or gas that is under greater pressure than atmospheric. Compression of a dry fluid may optionally be employed to allow for its delivery at low flow rates compared to those required to induce the same evaporative response to a dry fluid at atmospheric pressure.

A state of compression may result from the gas being pressurized into a static containment vessel, or may result by mechanically forcing, e.g., via a fan or blower, the gas through a conduit or port having reduced volume. For example, with reference to FIGS. 2 and 3, a compressed gas may be one that is forced along the first lumen 50 via a fan 100 through the fluid delivery ports. The gas may also be passed through a flow regulator 110 to further alter the pressure of the gas as it flows through fluid delivery ports 60. One in the art would understand that compression of the gas may be further regulated by the configuration and size of the exhaust ports. For example, reducing the number and size of the fluid delivery ports 60 reduces the pressure of the gas in the first lumen 50.

In various embodiments, the pressure of the compressed gas, if employed, is regulated above atmospheric pressure, for example above about 10-15 psi. For example, the gas may be regulated to about 10, 15, 20, 25, 30, 35, 40, 45, 50, 55, 60, 65, 70, 75, 80, 85, 90, 95, 100, 105, 110, 115, 120, 125, 130, 135, 140, 145, 150 psia or greater. To assist in regulating the pressure of the compressed gas, the fluid source 20 may be a compressed gas source. Additionally, the device may further include one or more valves disposed along the conduit 10 to regulate pressure and flow of the gas.

Figure 3:
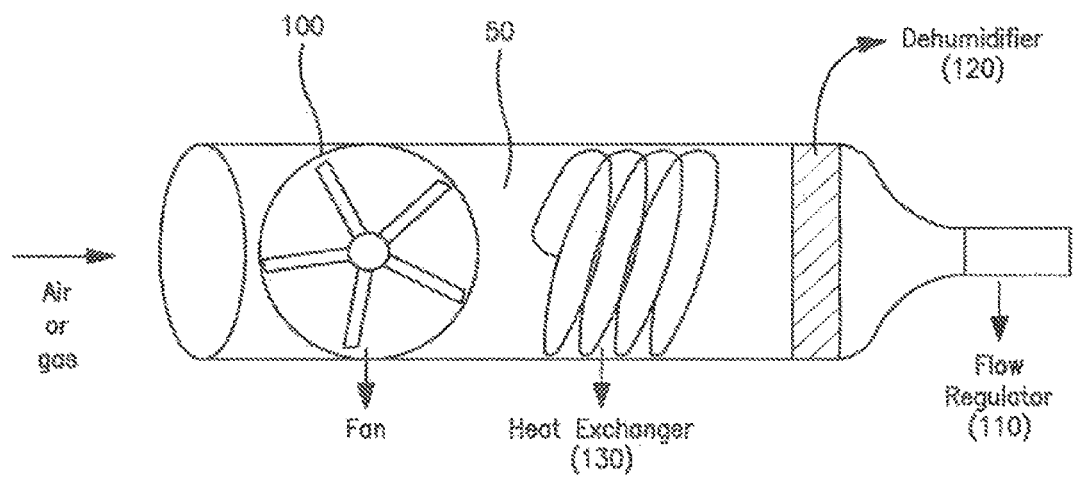
FIG. 3 illustrates a diagram of a portion of a cooling device of the present invention, according to an embodiment.

As shown in FIG. 3, the device may further include a dehumidifier 120 to assist in regulating the humidity of the gas.

As discussed herein, the invention is based in part on the physiological evaporative response to dry fluid, such as gas flow. Warm high flow of warm dry gas has been shown herein to be associated with a greater degree of cooling. As such, as shown in FIG. 3, the device may further include a heat exchanger 130 to regulate the temperature of the gas. As used herein, the term "warm" refers to a temperature of room temperature or greater. As such warm air may be greater than about 20, 21, 22, 23, 24, 25, 26, 27, 28, 29, 30, 31, 32, 33, 34, 35, 36, 37, 38, 39, 40° C. or greater.

In one embodiment, delivery of cooler gas is envisioned where a lower rate of evaporation is desired, for example when a longer duration of therapy is desired. As such the gas or air may be greater than about 0, 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40° C. In preferred embodiments of the invention, however, the dry fluid will be at normal body temperature (e.g., for humans, 37° C.) or warmer to a clinically acceptable temperature, with dry fluid at the ambient environmental temperature being particularly suitable for ambulatory settings, especially in emergency contexts.

Without being bound by a particular theory, the temperature of the gas is likely less significant than other factors, such as flow rate and relative humidity, since the specific heat capacity of a gas is low.

Figure 4:
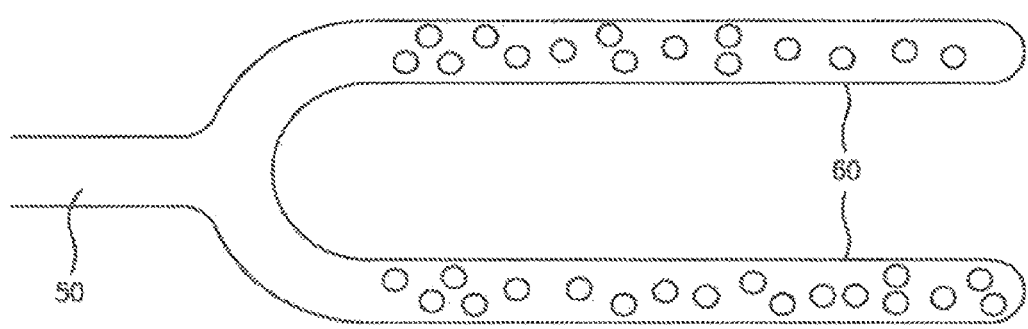
FIG. 4 illustrates a diagram of a portion of a cooling device of the present invention, according to an embodiment.
Figure 5:
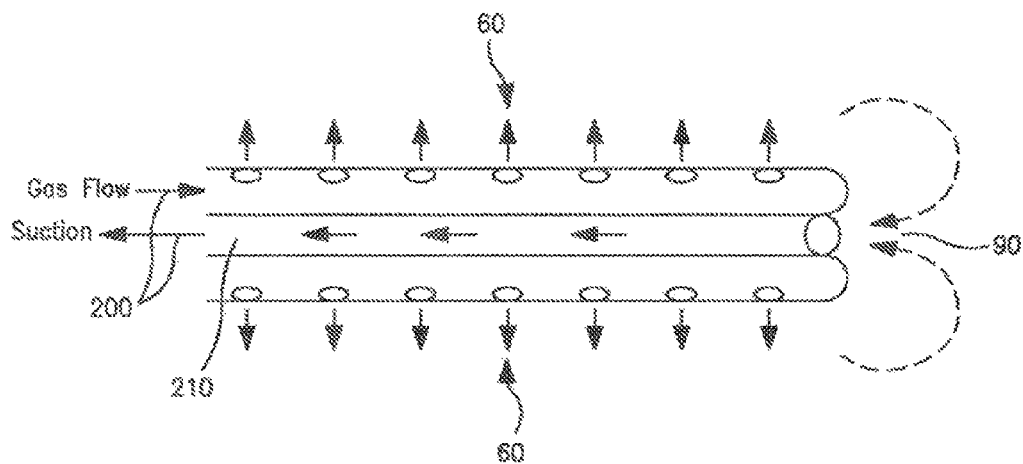
FIG. 5 illustrates a diagram of a portion of a cooling device of the present invention, according to one embodiment.
Figure 6:
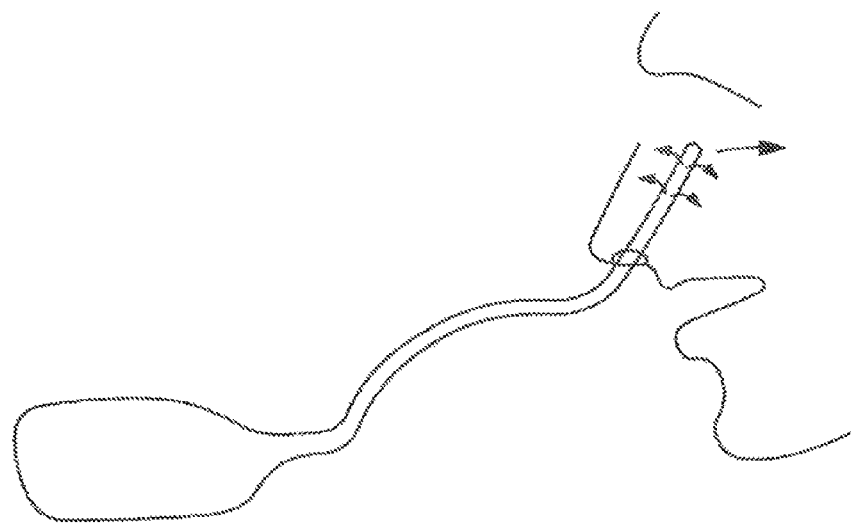
FIG. 6 illustrates a diagram of a cooling device and methodology of the present invention, according to an embodiment.
Figure 7:
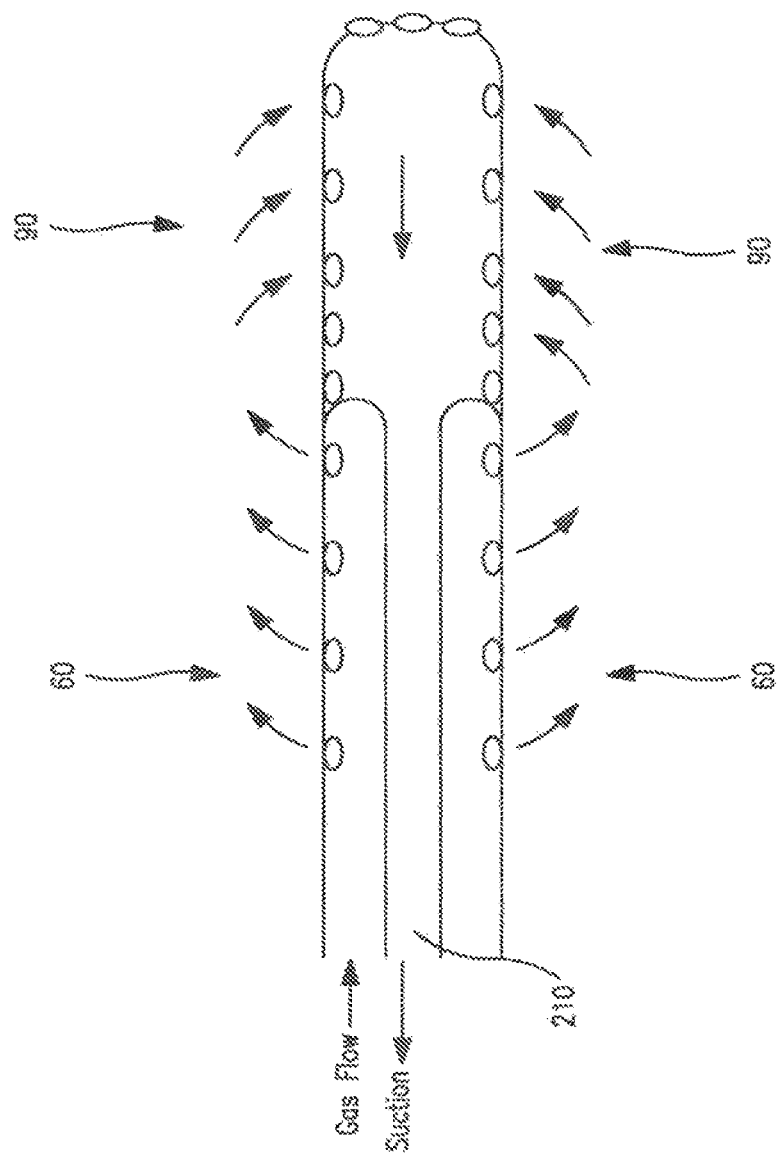
FIG. 7 illustrates a diagram of a portion of a cooling device, according to an embodiment.

Any configuration of fluid delivery ports, alone or in combination with return ports is envisioned to achieve desired gas flow to result influd elimination, anatomic or systemic cooling, energy removal, metabolic rate adjustment and/or weight loss. As shown in FIGS. 4, 5, and 7, fluid delivery ports may be configured in a variety ways to achieve a desired gas flow, in part depending of the shape of the bodily fluid-containing space or surface. FIG. 4 shows an embodiment in which the first lumen is bifurcated at the distal end to produce a fork shaped tip having parallel rows of fluid delivery ports 60. It is envisioned that the first lumen 50 may be split to provide any number of parallel (or non-parallel) rows of fluid delivery ports, for example 2, 3, 4, 5, 6, 7, 8 or greater rows. In alternative embodiments, it is envisioned that multiple rows of fluid delivery ports may also be created by including additional lumens as discussed further herein.

As shown in FIGS. 5 and 7, a desired gas flow may also be achieved by particular configurations of fluid delivery ports 60 in relation to return ports 90. FIG. 5 shows an embodiment having 3 distal lumens. Two lumens 200 deliver gas through fluid delivery ports 60, while one lumen 210 includes a single return port 90. In this configuration gas expands out of fluid delivery ports 60 into or on a bodily fluid-containing space or surface and is directed into lumen 210 through return port 90 via suction applied to lumen 210. FIG. 7 shows an embodiment having multiple return ports 90 disposed distal to the fluid delivery ports 60. In this configuration gas expands out of fluid delivery ports 60 into or on a bodily fluid-containing space or surface and is direct into lumen 210 through return ports 90 via suction applied to lumen 210.

The device may include a number of additional features to assist in regulating gas flow and pressure to achieve fluid elimination, anatomic or systemic cooling, energy removal, metabolic rate adjustment and/or weight loss. As shown in FIG. 2, the device may further include a temperature sensor 95 and/or pressure sensor 96. Such features allow the device to include dynamic feedback to control temperature, pressure and gas flow through the device and thus within, for example the bodily fluid-containing space to optimize evaporation of the bodily fluid, such as mucus to achieve fluid elimination, anatomic or systemic cooling, energy removal, metabolic rate adjustment and/or weight loss. For example, the temperature of the gas as it exits through the fluid delivery ports 60 may be regulated by controlling the pressure of the gas as it exits, as well as regulation of the gas flow by feedback provided by the temperature sensor 95. A temperature sensor which regulates delivery of the dry fluid in a feedback response based on the mammal's measured temperature (of the body or at the site of the targeted anatomical feature) may also be provided.

Pressure sensor 96 is placed at the distal tip to monitor pressure and includes means, such as a pressure transducer to adjust gas flow via feedback along with the temperature sensor 95. Following decompression and expansion of the gas through fluid delivery ports 60, the gas exits the bodily fluid-containing space by means of lumen 80. The flow out through the lumen 80 may be regulated by the feedback from the pressure sensor via a suction apparatus in fluid connection with the proximal end of lumen 80.

As discussed throughout, the fluid flow may be regulated by a number of features, alone or in combination, e.g., sensors, port size and number, gas pressure, and the like. The invention may utilize high flow of gas, which includes flow rates of between about 20 and 200 L/min, 40 and 130 L/min, or 20 and 80 L/min. For example, gas may be delivered at a flow rate of greater than about 10, 15, 20, 25, 30, 35, 40, 45, 50, 60, 65, 70, 75, 80, 85, 90, 95, 100, 105, 110, 115, 120, 125, and 130 L/min. As discussed herein, the flow rate may be varied throughout the duration of delivery to maximize evaporation within or on the bodily fluid-containing space or surface.

In various embodiments, the device may further include additional lumens to facilitate additional configurations of the expansion and return ports. As discussed above, multiple lumens may be provided to deliver gas through multiple fluid delivery ports. Similarly, multiple lumens may be provided to expel gas from the bodily fluid-containing cavity through multiple return ports. Various combinations are envisioned depending on the desired gas flow.

The duration of treatment will vary depending on the desired level of fluid elimination, anatomic or systemic cooling, energy removal, metabolic rate adjustment and/or weight loss.

It has been established that the reduction in core temperature is related to the flow rate and dryness of the gas, wherein an increase in flow rate and decrease in dryness increases the core cooling rate. As such, an appropriate technique for determining the desired duration to provide cooling treatment is determined by monitoring the core body temperature. Typically the gas is delivered for a duration to lower core body temperature of the mammal between about 2 to 4° C. However, the core body temperature may be lowered by longer delivery of gas. Additionally, it will be understood that once reached, a specific core body temperature may be maintained by adjusting the flow rate, pressure, temperature and humidity of the gas.

Where the desired result is fluid elimination, the duration of treatment may be determined by monitoring flow rate, temperature and change in humidity level (from inlet to exhaust). Where the desired result is energy removal/metabolic rate adjustment/weight loss, the duration of treatment may be determined a similar approach. In the case of metabolic rate adjustment to promote weight loss, the invention may be used overnight over a longer period of time. The gas flow rate may be set at a lower flow rate, e.g., between 20 and 40 L/min, to improve tolerability. The therapy can also be intermittently paused to allow the mucus-containing space or surface to recover, if needed.

In various embodiments, the gas is delivered to a bodily fluid-containing space or surface. Such spaces and surfaces may include, but are not limited to the lungs, trachea, oral cavity, nasopharynx, nostrils, gastro-intestinal system, stomach, peritoneal cavity, skin and urinary bladder. In various embodiments, the body fluid-containing space or surface is a mucus-containing space or surface, for example, any space or surface that secretes or includes mucus, such as mucosal membranes or cells. For example, with reference to FIGS. 1 and 6, the bodily fluid-containing space or surface is the nasal or pharynx cavity. In this embodiment, the device in configured to be introduced into the nasal cavity and may include any of the features as shown in FIGS. 1-7. In this configuration, gas is expanded through the fluid delivery ports and cooling is achieved in part due to the physiological evaporative response to dry gas air flow. Introduction of the dry air into the nasal cavity causes release of bodily fluid, such as mucus from the mucus membranes, whose subsequent evaporation produces vasodilation, evaporative heat loss and cooling of the blood in the carotid arteries as well as conductive cooling of the brain stem. In some embodiments, drugs that enhance mucus production are administered to the mammal.

In various embodiments, one being where the bodily fluid-containing space or surface is the nasal or pharynx cavity, the return ports are configured such that air flow is unidirectional from the expansion ports to the return ports to avoid heat loss of the gas back to the body.

As such, the term "bodily fluid" may encompass a variety of different fluid types. Such fluids may include, but are not limited to mucus, saliva, gastric fluid, urine, sweat and the like.

Figure 8:
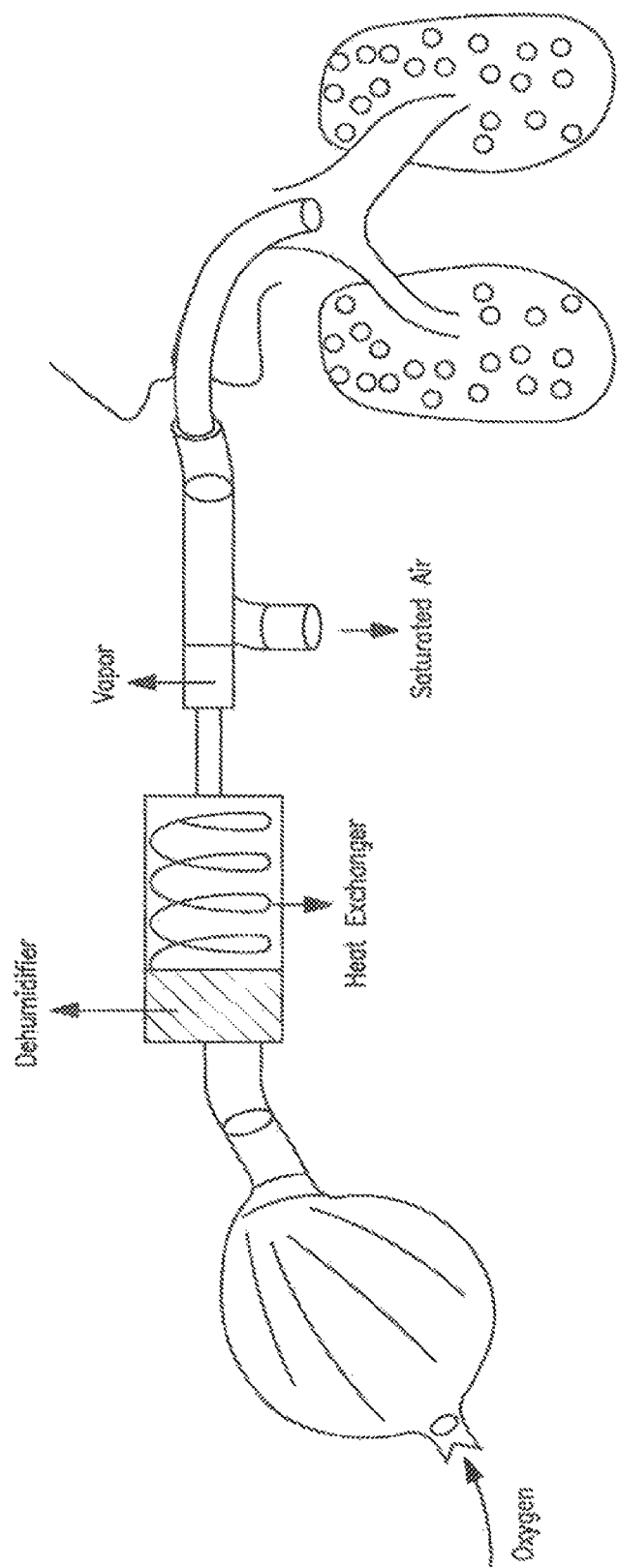
FIG. 8 illustrates a diagram of a cooling device and methodology of the present invention, according to an embodiment.
Figure 10:
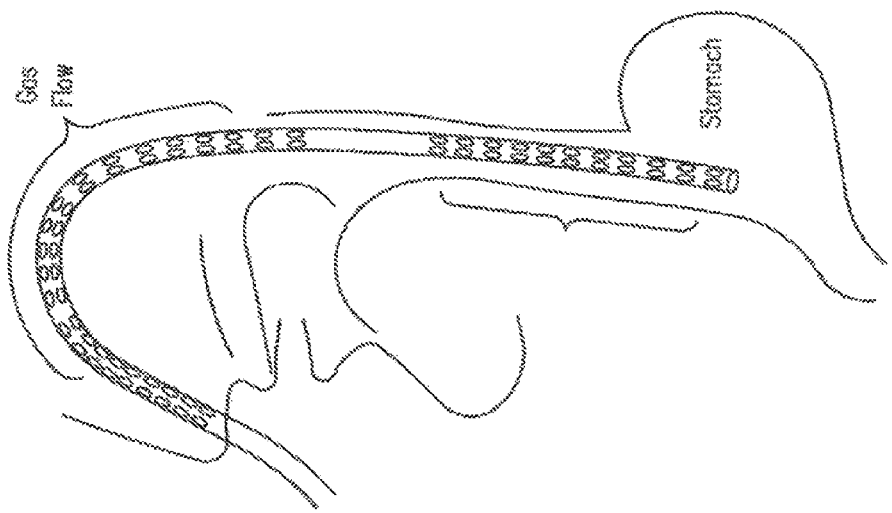
FIG. 10 illustrates a diagram of a portion of a cooling device and methodology of the present invention, according to an embodiment.
Figure 9:
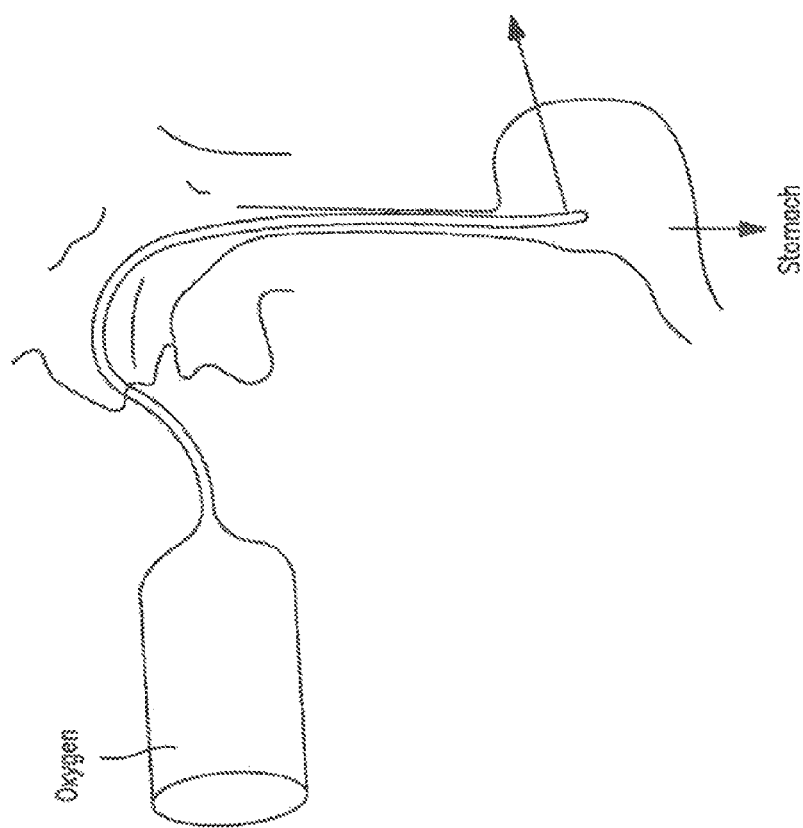
FIG. 9 illustrates a diagram of a cooling device and methodology of the present invention, according to an embodiment.

Evaporative cooling may be achieved in or on a variety of bodily fluid-containing spaces or surfaces. In one embodiment, the device may be configured to deliver gas to the pulmonary bed of the lungs to achieve cooling and neuroprotection, FIG. 8 shows an embodiment of a device for use in delivering gas to the lungs through the oral cavity. However, it is envisioned that the lungs may also be accessed via the nasal cavity. Additionally, various configurations are envisioned such as a forked conduit allowing for independent delivery and expulsion of gas in each of the left and right lungs. FIGS. 9 and 10 show embodiments in which the device is configured to deliver gas to the stomach. As shown in FIG. 9, in one embodiment, the fluid delivery ports are disposed proximal to the return ports such that gas flows from the nasopharynx cavity to the stomach. Other port configurations are envisioned such as providing both expansion and return ports in the stomach cavity.

In another embodiment, the device is configured to deliver gas to the mouth or oral cavity. In this embodiment, the device may be configured with or without return ports. When no return ports are desired, the delivered gas is allowed to exit exhaust from the mouth which may be mechanically held open.

In various embodiments, the device may include additional features known in the art to assist in placement of the conduit into the desired cavity. For example, the device may further include one or more inflation balloons disposed along the conduit which may be inflated by an appropriate inflation fluid provided by one or more lumens incorporated into the conduit.

In various embodiments, the conduit may be incorporated into a variety of conventional medical devices. For example, the conduit may be incorporated into a respiratory mask or nebulizer for delivery of air into the nasopharyngeal and/or pharyngeal regions of the nasal cavity. Such devices may be adapted to provide ambient air or another suitable dry fluid supplied in a kit. Alternatively, the conduit may be incorporated into a cannula, catheter, nasal pillow or the like depending on the location of the surface or cavity being accessed.

In various embodiments, the method and device of the invention are useful for rapid emergency use (e.g., cardiac arrest, stroke, heat stroke, heat exhaustion, etc.) since the device and method are easy to implement, non-invasive, non-toxic, effective, and do not interfere with current standard of care. For example, in one embodiment to treat stroke victims, the device may employ ambient air drawn by a vacuum or other suction means through a device having expansion and return ports introduced into the nasal passage. In both a related or alternative embodiment, as discussed herein, compressed dry gas from a compressed gas source may be introduced into the device.

Although the invention has been described with reference to the above example, it will be understood that modifications and variations are encompassed within the spirit and scope of the invention. Accordingly, the invention is limited only by the following claims.

EXAMPLE 1

Nasal Cooling in Porcine Subjects

This example illustrates the effect of high flow nasal dry air on the cortical and core body temperature in intubated adult pigs, modeling human responses.

Core Body and Brain Temperature During High Flow Dry Air in Intubated Pigs:

Four adult male pigs (70 pound) were anesthetized and intubated. Thermocouples were placed in the right atrium and the lateral ventricles through a temporal burr hole. Compressed dry air was delivered through the custom nasal cannula at 80 to 100 L/min for 10 minutes. FIG. 11 shows simultaneous recordings of core temperature from the right atrium (top) and the brain temperature from the lateral cerebral ventricles (bottom). The brain temperature decreased from 35.9±0.3° C. to 32.3±0.4° C. over 10 minutes. During the same time period, the core body temperature decreased from 35.8±0.7° C. to 35.2±0.4° C. The brain temperature promptly returned to baseline within 10±1.3 minutes of cessation of the airflow. For a given flow rate, the rate of temperature change was similar within the same animal and among all four animals.

Effect of Air Flow Rate on Brain Temperature:

In two adult pigs, the effect of airflow rate on the rate of brain cooling was evaluated. FIG. 12 shows recorded mean temperatures at various airflow rates tested.

At airflow rates used clinically (20 L/min), no appreciable change was observed in the brain temperatures. Flow-rates of 150 L/min and 300 L/min were indistinguishable and flow rate of 100 L/min showed intermediate results. In both animals at flow rates of >100 L/min, moderate brain hypothermia (<34° C.) could be achieved in approximately 10 minutes.

Core Body Hypothermia Using High Flow Dry Air: At higher flow rates (150 L/min and 300 L/min), a progressive decrease in core body temperature was observed. It is expected that that prolonged exposure to high flow dry air will lead to core body hypothermia. The brain temperature declined similar to prior experiments and achieved a plateau temperature of 30.1±0.4° C., however, the body temperature continued to decline and reached a minimal value of 31.8±0.8° C. over 30 minutes. Cessation of airflow resulted in a gradual incomplete recovery of baseline temperature to 34.5±0.8° C. (baseline 35.6±0.6° C.) for the brain and 35.1±0.2° C. (baseline 35.5±0.8° C.) for the body over the next 30 minutes. No significant changes were observed either in the blood pressure, heart rhythm or the heart rate in all the four animals.

This example demonstrates the feasibility of the present invention to reproducibly induce brain and core body hypothermia in intubated pigs using high flow of a gas (air) through the nostrils. The rate of hypothermia using this approach appears superior to published cooling rates using other ambulatory hypothermia methods and devices as shown in FIG. 13. FIG. 13 demonstrates that high-flow dry air resulted in superior rates of brain cooling compared with both nasal coolant perflurocarbon (PFC) using the Rhino-Chill™ device or irrigation of ice cold saline in the nasopharynx.

What is claimed is:

1. A method for promoting weight loss in a mammal, comprising delivering a dehumidified fluid not including a coolant into or upon a bodily fluid-containing space or surface to provide evaporation of a bodily fluid upon contact with the dehumidified fluid.

2. A method for inducing controlled evaporation of a body fluid from a bodily fluid-containing space or surface of a mammal, comprising delivering a dehumidified fluid not including a coolant into or upon the bodily fluid-containing space or surface to provide evaporation of the bodily fluid upon contact with the dehumidified fluid, wherein drugs that enhance mucus production are administered to the mammal.

3. A method for inducing controlled evaporation of a body fluid from a bodily fluid-containing space or surface of a mammal, comprising delivering a dry fluid not including a coolant into or upon the bodily fluid-containing space or surface to provide evaporation of the bodily fluid upon contact with the dry fluid and administering drugs that enhance mucus production to the mammal.

* * * * *